(12) United States Patent
Haider et al.

(10) Patent No.: US 7,166,086 B2
(45) Date of Patent: Jan. 23, 2007

(54) SUBSTANCE DELIVERY VIA A ROTATING MICROABRADING SURFACE

(75) Inventors: M. Ishaq Haider, Morrisville, NC (US); Alexander G. Lastovich, Raleigh, NC (US); Timothy J. Erskine, Sandy, UT (US); John A. Mikszta, Durham, NC (US); Frank E. Martin, Durham, NC (US); Scott A. O'Connor, Durham, NC (US); Jason B. Alarcon, Durham, NC (US); John P. Dekker, III, Cary, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 210 days.

(21) Appl. No.: 10/649,134

(22) Filed: Aug. 27, 2003

(65) Prior Publication Data

US 2004/0143211 A1    Jul. 22, 2004

Related U.S. Application Data

(60) Provisional application No. 60/406,694, filed on Aug. 29, 2002.

(51) Int. Cl.
*A61B 17/20* (2006.01)

(52) U.S. Cl. .................................. 604/46; 604/290

(58) Field of Classification Search ............ 604/46–48, 604/174, 500, 289–290; 606/185–186, 167–173, 606/176–183; 601/19
See application file for complete search history.

(56) References Cited

U.S. PATENT DOCUMENTS

| | | | |
|---|---|---|---|
| 3,756,242 A | 9/1973 | Coss | |
| 3,918,449 A * | 11/1975 | Pistor | ............................ 604/47 |
| 3,964,482 A | 6/1976 | Gerstel et al. | |
| 5,003,987 A | 4/1991 | Grinwald | |
| 5,250,023 A | 10/1993 | Lee et al. | |
| 5,611,806 A | 3/1997 | Jang | |
| 5,618,295 A * | 4/1997 | Min | ............................ 606/171 |
| 5,679,647 A | 10/1997 | Carson | |
| 5,843,114 A | 12/1998 | Jang | |
| 5,879,326 A | 3/1999 | Godshall et al. | |
| 5,964,729 A | 10/1999 | Choi et al. | |
| 5,983,136 A | 11/1999 | Kamen | |

(Continued)

FOREIGN PATENT DOCUMENTS

EP          0381410         1/1990

(Continued)

*Primary Examiner*—Nicholas Lucchesi
*Assistant Examiner*—Theodore J. Stigell
(74) *Attorney, Agent, or Firm*—Robert E. West

(57) ABSTRACT

A method and device for the delivery of a substance into skin via the rotational movement of a microabrader device reduces the effects of operator variability. The method includes applying a substance to an area of a patient's skin through the rotational movement of microprotrusions which may be imparted by a spring device present in the microabrader device or the motion of the operator through the handle of the microabrader device. The device may further include system and methods for monitoring pressure of the device against the skin and thereby promote consistency between applications and control of penetration depth. The delivered substance may be placed on the microprotrusions and a reconstituting liquid included in the microabrader device.

24 Claims, 12 Drawing Sheets

U.S. PATENT DOCUMENTS

| | | |
|---|---|---|
| 6,050,988 A | 4/2000 | Zuck |
| 6,083,196 A | 7/2000 | Trautman et al. |
| 6,183,434 B1 | 2/2001 | Eppstein |
| 6,230,051 B1 | 5/2001 | Cormier et al. |
| 6,256,533 B1 | 7/2001 | Yuzhakov et al. |
| 6,322,808 B1 | 11/2001 | Trautman et al. |
| 6,331,266 B1 | 12/2001 | Powell et al. |
| 6,334,856 B1 | 1/2002 | Allen et al. |
| 6,440,096 B1 | 8/2002 | Lastovich et al. |
| 6,503,231 B1 | 1/2003 | Prausnitz et al. |
| 6,537,242 B1 | 3/2003 | Palmer |
| 6,537,264 B1 | 3/2003 | Cormier et al. |
| 6,558,361 B1 | 5/2003 | Yeshurun |
| 6,562,014 B2 | 5/2003 | Lin et al. |
| 6,595,947 B1 | 7/2003 | Mikszta et al. |
| 6,835,184 B1 | 12/2004 | Sage et al. |
| 2002/0010412 A1 | 1/2002 | Eppstein |
| 2002/0077584 A1 | 6/2002 | Lin et al. |
| 2002/0091357 A1 | 7/2002 | Trautman et al. |
| 2002/0188245 A1 | 12/2002 | Martin et al. |
| 2003/0093040 A1* | 5/2003 | Mikszta et al. ............. 604/289 |
| 2004/0064087 A1 | 4/2004 | Lastovich et al. |
| 2004/0077994 A1 | 4/2004 | Lastovich et al. |
| 2004/0087992 A1* | 5/2004 | Gartstein et al. ........... 606/186 |

FOREIGN PATENT DOCUMENTS

| | | |
|---|---|---|
| EP | 1 086 719 | 8/2000 |
| EP | 1086719 A1 * | 3/2001 |
| WO | WO 95/12357 | 5/1995 |
| WO | WO 96/17648 | 6/1996 |
| WO | WO 97/48440 | 6/1997 |
| WO | WO 02/02180 | 1/2002 |
| WO | WO 02/32331 | 4/2002 |

* cited by examiner

SUBSTANCE DELIVERY VIA A ROTATING MICROABRADING SURFACE

RELATED APPLICATIONS

This application claims priority to U.S. Provisional Patent Application No. 60/406,694, filed Aug. 29, 2002, which is hereby incorporated by reference in its entirety. This application is also related to U.S. application Ser. No. 10/649,396 filed Aug. 27, 2003, and U.S. application Ser. No. 10/649,395 filed Aug. 27, 2003.

FIELD OF THE INVENTION

The present invention relates to a method and device for abrading the skin. More particularly, the invention is directed to a method of abrading the stratum corneum by employing a device imparting a rotary movement to an abrading surface.

BACKGROUND OF THE INVENTION

Delivery of substances to the body through the skin has typically been invasive, involving needles and syringes to facilitate intradermal (ID), intramuscular (IM) or subcutaneous (SC) injection. These methods are painful for the subject, require the skills of a trained practitioner and often produce bleeding. There have been efforts to overcome these disadvantages by use of devices which abrade the stratum corneum, the thin external layer of keratinized cells about 10–20 µm thick. The bioactive substance is delivered to the exposed viable epidermis.

This technique avoids the nerve net and places the bioactive substance in close proximity to blood vessels and lymphatics for absorption and delivery of the substance throughout the body.

For topical delivery of vaccines, the epidermis itself is a particularly desirable target as it is rich in antigen presenting cells. In comparison, the dermal layer below the epidermis contains fewer antigen presenting cells. Furthermore, the stratum corneum and epidermis do not contain nerves or blood vessels, so this method has the advantage of being essentially painless and blood-free while giving access to the skin layers capable of responding to the antigen.

The prior art reports a variety of devices and methods for disrupting the stratum corneum for the purpose of delivering substances to the body. For example, breach of the stratum corneum may be achieved by puncturing as taught in U.S. Pat. No. 5,679,647 to Carson, et al. This patent teaches that narrow diameter tines, such as those found on devices used for tuberculin skin tests and allergy tests, can be coated with polynucleotides or oligonucleotides and used for delivery of such materials into the skin. The method of using such devices involves puncturing the skin with the tines resulting in intracutaneous injection of the coated substance.

U.S. Pat. No. 5,003,987; U.S. Pat. No. 5,879,326; and U.S. Pat. No. 3,964,482 teach breaching the stratum corneum by cutting.

SUMMARY OF THE INVENTION

The present invention is directed to a method and device for the rotational abrading of the skin, and particularly, the stratum corneum of the skin. The invention is further directed to a method of obtaining a sample from or for the delivery of a substance into the skin, such as a drug or pharmaceutical agent, through the rotational abrading of an area on the stratum corneum.

Substances to be delivered particularly include bioactive substances, including pharmaceutical agents, medicaments, vaccines and the like. Substances may be in solid or liquid form, depending on formulation and delivery method. They can be delivered, inter alia, in the form of dry powders, gels, solutions, suspensions, and creams. Particularly preferred medicaments for delivery by the methods of the invention include vaccines, allergens and gene therapeutic agents.

One aspect of the invention is directed to a method and device for preparing a delivery site on the skin to enhance the delivery of a pharmaceutical agent through the stratum corneum of the skin to a sufficient depth where the pharmaceutical agent can be absorbed and utilized by the body. Such preparation is accomplished by the use of a device to impart a rotational movement to the entire microabrading device or the abrading surface of a microabrading device to disrupt the stratum corneum.

Dermal tissue represents an attractive target site for delivery of vaccines and gene therapeutic agents. In the case of vaccines (both genetic and conventional), the skin is an attractive delivery site due to the high concentration of antigen presenting cells (APC) and APC precursors found within this tissue, especially the epidermal Langerhan's cells (LC). Several gene therapeutic agents are designed for the treatment of skin disorders, skin diseases and skin cancer. In such cases, direct delivery of the therapeutic agent to the affected skin tissue is desirable. In addition, skin cells are an attractive target for gene therapeutic agents, of which the encoded protein or proteins are active at sites distant from the skin. In such cases, skin cells (e.g., keratinocytes) can function as "bioreactors" producing a therapeutic protein, which can be rapidly absorbed into the systemic circulation via the papillary dermis. In other cases, direct access of the vaccine or therapeutic agent to the systemic circulation is desirable for the treatment of disorders distant from the skin. In such cases, systemic distribution can be accomplished through the papillary dermis.

The present invention provides a method and microabrader device to rotationally abrade the skin in conjunction with the delivery of a bioactive substance, including but not limited to nucleic acids, amino acids, amino acid derivatives, peptides or polypeptides. It has been discovered that nucleic acids exhibit enhanced gene expression and produce an enhanced immune response to the expressed protein when they are delivered simultaneously with abrasion of the stratum corneum. Similarly, allergens delivered simultaneously with abrasion produce a more vigorous immune response than conventional allergen testing methods.

In one preferred embodiment, the present invention comprises a microabrader for delivering a substance into the skin having a base with at least one abrading facet, to which an abrading surface having an arrangement of microprotrusions that have at least one scraping edge is attached, mounted or integral with, and a handle attachment facet, to which a handle or other grasping device is attached, mounted, or integral with. The handle may also be separated from, mated to, or integral with a mechanism capable of imparting a rotational movement to the entire device or only the abrading surface thereof. By "abrading surface" is meant the surface that is presented to the skin during the process of abrasion, including at least one microprotrusion, the surface area between such microprotrusion(s) and surrounding surface.

A circular or rotational abrasion of the skin may be achieved with a mechanical or externally powered rotary device including a microabrader device so that a localized area of skin is treated or abraded. The rotary device would comprise a housing in which the microabrader array is rotated against a subject's skin and an interlock mechanism that the user would deactivate to actuate the rotation of the rotary device. In one embodiment, the housing of the rotary device would keep the skin in place as pressure is applied to ensure that the microabrader array surface would abrade and/or tension the same area of a patient's skin and a spring or other component associated with the interlock mechanism would control the speed at which the abrading surface rotates against the skin. Consequently, this embodiment should ensure consistent, reproducible results as to the amount of substance absorbed into a body, especially in clinical settings.

According to another embodiment of the invention, the circular abrasion according to the method can be combined with monitoring the amount of pressure applied to the microabrader device (either visually, or in a rotary device) to maintain an approximate constant downward force to achieve a more consistent abrasion, and more efficiently deliver drug, vaccine, or medicament to a patient's body. For example, the technician and/or user can monitor the downward force being applied to the microabrader device during the rotary motion so that a consistent, appropriate downward force is applied. Thus, the technician using the microabrader device can apply the necessary pressure to achieve the same degree of stratum corneum disruption and depth of penetration on all patients. This may be especially important for delivery of certain classes of compounds, such as vaccines, in which the desired target area is the antigen-presenting cells within the epidermis and not the deeper dermal tissue and capillary beds.

The monitoring of the pressure can be achieved via a mechanical or electrical pressure gauge, a pre-tensioned spring, or an electronic pressure transducer. This monitoring device may be as simple as indicia or as sophisticated as an electronic piezoelectric film that detects the amount of pressure and indicates the amount of pressure.

The present invention also involves a method for delivering a substance to the skin comprising the use of a device that imparts a rotational movement to the microabrading device or microabrading surface on an area of the skin to produce furrows of sufficient depth to allow the substance, which is administered prior to, simultaneously with, or following the abrasion of the skin, to be taken up by the predetermined skin layer. By means of the present microabrader device the rotational movement combined with multiple passes of the device across the skin can result in progressively deeper furrows in the skin, thereby allowing delivery of a substance to a desired depth with in the skin.

BRIEF DESCRIPTION OF THE DRAWINGS

The invention is better understood by reading the following detailed description with reference to the accompanying figures, in which like reference numerals refer to like elements throughout, and in which.

DETAILED DESCRIPTION OF THE INVENTION

The primary barrier properties of the skin including the resistance to drug or vaccine delivery reside in the outermost layer of the epidermis, referred to as the stratum corneum. The inner layers of the epidermis generally include three layers, commonly identified as the stratum granulosum, the stratum malpighii, and the stratum germinativum. Once a drug or vaccine or other substance appears below the stratum corneum, there is essentially no resistance to diffusion into subsequent layers of the skin and eventual absorption by the body.

Delivering a substance into or through the viable epidermis can be an effective method for facilitating absorption of some substances, and particularly some vaccines, by the body. The present invention is primarily directed to a device and method for facilitating delivery of a substance, and particularly a pharmaceutical agent, into or through the viable epidermis so that more rapid absorption of larger quantities of the bioactive substance or pharmaceutical agent results.

As used herein, the term "abrade" refers to removing at least a portion of the stratum corneum to increase the permeability of the skin without causing excessive skin irritation or compromising the skin's barrier to infectious agents. This is in contrast to "puncturing" which produces discrete holes through the stratum corneum with areas of undisrupted stratum corneum between the holes.

As used herein, "penetrating" refers to entering the stratum corneum without passing completely through the stratum corneum and entering into the adjacent layers. This is not to say that that the stratum corneum cannot be completely penetrated to reveal the interface of the underlying layer of the skin. Piercing, on the other hand, refers to passing through the stratum corneum completely and entering into the adjacent layers below the stratum corneum.

The present invention is directed to a device and to a method for abrading the stratum corneum in a rotary or circular fashion for abrading the stratum corneum to enhance the administering of a substance through the stratum corneum of the skin of a patient.

The rotary method and the device for rotating a microabrader array surface according to the invention is capable of abrading the skin to increase the surface area within the epidermal layer and improve the efficacy of substance or drug or vaccine delivery into the body of the subject by either direct uptake by the antigen presenting cells (APC's), capillary drainage, or the lymphatic drainage phenomenon. In preferred embodiments, the device is capable of abrading the skin thereby penetrating the stratum corneum without piercing the stratum corneum.

Figure 4:
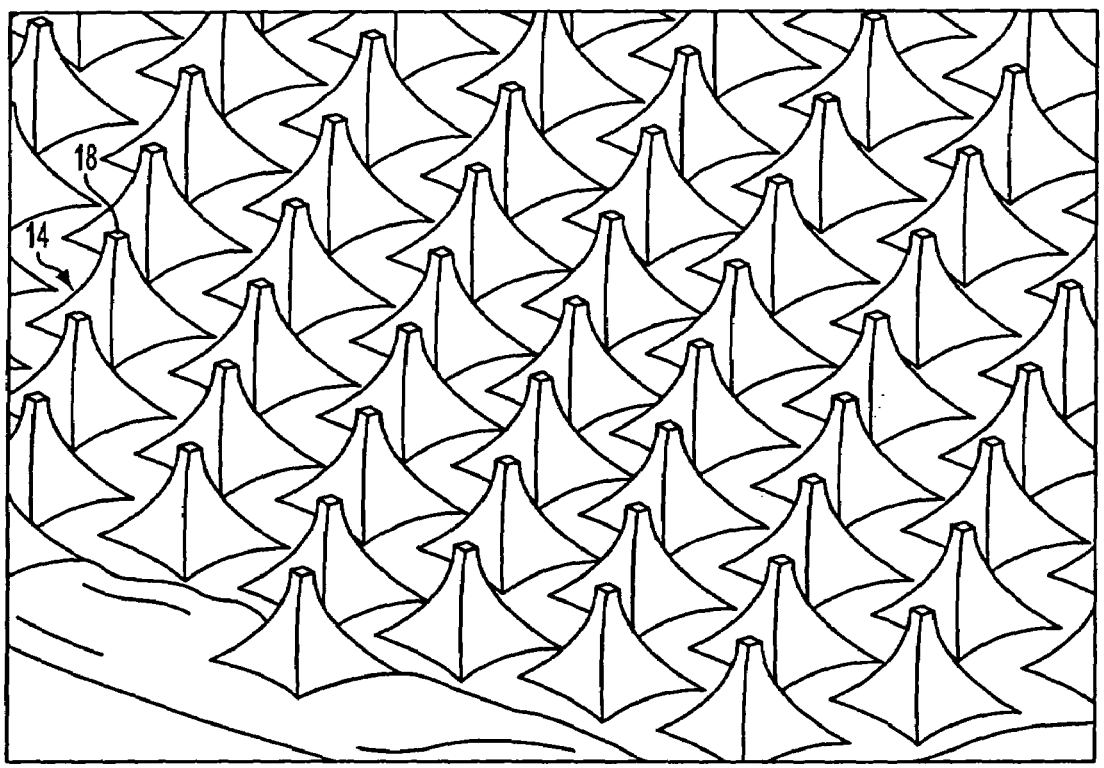
FIG. 4 is a microphotograph of an abrading surface.
Figure 5:
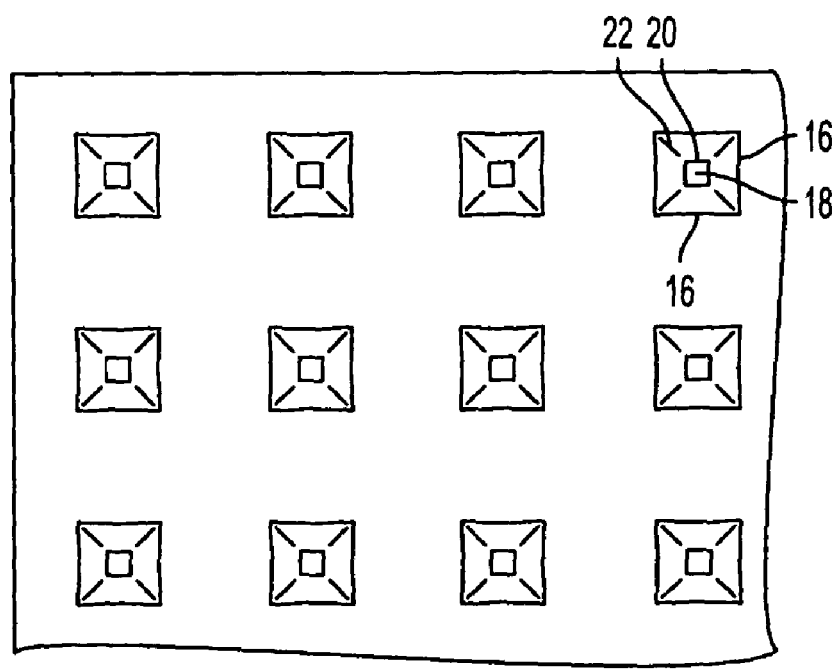
FIG. 5 is a bottom view of the abrading surface of the embodiment of FIG. 3.

Preferably, an abrading surface comprising a desired array of microprotrusions is rotated against a desired skin area. The resultant circular abrasion of the skin according to the invention disrupts the stratum corneum increasing the surface area of the viable epidermal layer so that a greatly increased dose concentration of the substance delivered is achieved. The controlled circular motion and abrasion tends to keep the dose within the rotary or circular abraded area. Consequently, the dose can be limited to a smaller area by using the circular or spin delivery according to the invention resulting in increased substance delivered to a limited portion of the body, as the substance is not pushed away from the application site. For example, the substance can be contained in a 1 $cm^2$ circle, according to one embodiment of the invention. That is, the area abraded by using a substantially straight, back and forth technique can be about 2 times larger than an area abraded using the circular technique. Depending upon the subject or the substance being delivered, a smaller or larger abrading area may be used and delivered in a circular fashion and a smaller area will be abraded than with the same abrading surface when using a straight technique.

The substance to be administered using the methods of this invention may be applied to the skin prior to abrading, simultaneous with abrading or post-abrading. According to one embodiment of the methods of the invention, however, certain or specific bioactive substances, including nucleic acid-based vaccines and peptides or polypeptides, are applied to the skin prior to or simultaneously with abrasion rather than being applied to previously abraded skin. That is, certain substances when abraded into the skin rather than being passively applied to previously abraded skin result in improved response.

The substance may be delivered into the skin in any pharmaceutically acceptable form. In one embodiment, the substance is applied to the skin and an abrading device is then forced against the skin while being twisted or moved in a circular fashion over the skin and the substance. It is preferred that the minimum amount of downward force to produce the abrasion that achieves the desired result be used. The amount of force and rotation to achieve the necessary abrasion to achieve efficient delivery depends upon the drug or vaccine to be delivered. One of ordinary skill in the art would be able to determine the appropriate amount of force and rotation (and thus, the resultant abrasion) to achieve the appropriate amount of drug or vaccine delivery through routine experimentation.

In one embodiment, the substance may be applied in dry form to the abrading surface or an adjacent surface thereto or even contained within a storage reservoir of, or within the delivery device prior to application. In this embodiment, a reconstituting liquid can applied to the skin at the delivery site prior to or simultaneously with the application of the substance-coated abrading device. The abrading surface is then rotated against or rubbed in a circular fashion over the skin so that the substance concurrently or subsequently becomes dissolved in the reconstituting liquid on the surface of the skin and is delivered simultaneously with abrasion. Alternatively, a reconstituting liquid may be contained in the abrading device and released to dissolve the substance as the device is applied to the skin for abrasion. Due to the containment of the abrader in a smaller area when using a circular abrading motion, the volume of reconstitution liquid may also be reduced, depending upon the needs of the substance to be applied.

According to the invention, skin disruption, for example, furrows or other openings will be formed in a circular fashion on the skin of a subject. If the microabrader abrading surface area is composed of a rectangular, square or other arrays of microprotrusions that results in intersecting furrows when the microabrader device is rotated or twisted, this intersection of furrows suggests that the reconstituting liquid will have more grooved areas within the abraded area and thus may minimize the amount of liquid lost due to the centrifugal force of the rotating microabrader abrading surface. In addition to the greater amount of furrows in the abrading skin, a more tortuous path is created which likewise suggests the liquid will tend to remain in the abraded area. Thus, the circular abrasion method may possibly employ a lower volume of reconstitution liquid and suggests a reduction of substance loss since the abrader will form furrows that capture the substance and possibly present an increase surface area for uptake of the substance, thereby avoiding the urging away of the substance as known in prior abrading methods.

As shown in FIG. 1, a manual microabrader device 2 includes base 4 onto which an abrading surface 5 can be mounted. Preferably, base 4 is a solid molded piece. In one embodiment, base 4 is configured with a mushroom-like crown **4*b* that curves upward and is truncated at the top. The top of base 4 is generally flat with abrading surface 5 being mounted thereon. Alternatively, the truncated top may have a recess for receiving abrading surface 5. In all embodiments, abrading surface 5 includes a platform 12 with an array of microprotrusions 14 (FIG. 3) that are affixed or otherwise integrally extends above the platform 12**.

Referring to FIG. 2, in one embodiment of the microabrader device 10, not shown, of the invention, includes a conforming abrading surface support 12 having a plurality of microprotrusions 14 extending from the bottom surface of the support. The support generally has a thickness sufficient to allow attachment of the surface to the base of the microabrader device. Alternatively, a differing microabrader device 10 can be attached to or be integral with the top surface of the abrading surface support 12. The dimensions of the abrading surface support 12 can vary depending on the length of the microprotrusions, the number of microprotrusions in a given area, the three-dimensional contour (planar, stepped, lenticular, arcuate, etc.) of the microprotrusions, the amount of the substance to be administered to the patient's skin 28, and the microabrader device to which it is attached or integrally formed with. Typically, the abrading surface support 12 has a surface area of about 1 to 4 $cm^2$. In one preferred embodiments, the abrading surface support 12 has a surface area of about 1 $cm^2$.

As shown in FIGS. 2, 3, 4 and 5, the microprotrusions 14 project from the surface of the abrading surface support 12 and are substantially perpendicular to the plane of the abrading surface support 12. The microprotrusions in the illustrated embodiment are arranged in a plurality of rows and columns and are spaced apart a uniform distance. Alternatively, the microprotrusions may be non-uniformly spaced apart in a pattern, or may be randomly spaced. The microprotrusions 14 of one embodiment, have a generally pyramid shape with sides 16 extending to a tip 18. The sides 16 as shown have a generally concave profile when viewed in cross-section and form a curved surface extending from the abrading surface support 12 to the tip 18. In the embodiment illustrated, the microprotrusions are formed by four sides 16 of substantially equal shape and dimension. As shown in FIGS. 4 and 5, each of the sides 16 of the microprotrusions 14 have opposite side edges contiguous with an adjacent side and form a scraping edge 22 extending outward from the abrading surface support 12. The scraping edges 22 define a generally triangular or trapezoidal scraping surface corresponding to the shape of the side 16. In further embodiments, the microprotrusions 14 can be formed with fewer or more sides.

The microprotrusions 14 preferably terminate at blunt tips, or mesas 18. Generally, the mesa 18 is substantially flat and parallel to the support 14. When the base of the microprotrusion is wider than the tip 18, the total length of the microprotrusions do not penetrate the skin; thus, the length of the microprotrusions is greater than the total depth to which said microprotrusions penetrate said skin. The mesas 18 preferably form a well-defined, sharp edge 20 where it meets the sides 16. The edge 20 extends substantially parallel to the abrading surface support 12 and defines a further scraping edge. In further embodiments, the edge 20 can be slightly rounded to form a smooth transition from the sides 16 to the mesa 18. Preferably, the microprotrusions are frustoconical or frustopyramidal in shape.

The microabrader device 10 and the microprotrusions can be made from a plastic material that is non-reactive with the substance being administered. A non-inclusive list of suitable plastic materials include, for example, polyethylene, polypropylene, Poly methyl methacrylate (PMMA), polyamides, polystyrenes, polyesters, and polycarbonates as known in the art. Alternatively, the microprotrusions can be made from a metal such as stainless steel, tungsten steel, alloys of nickel, molybdenum, chromium, cobalt, titanium, and alloys thereof, or other materials such as silicon, ceramics and glass polymers. Metal microprotrusions can be manufactured using various techniques similar to photolithographic etching of a silicon wafer or micromachining using a diamond tipped mill as known in the art. The microprotrusions can also be manufactured by photolithographic etching of a silicon wafer using standard techniques as are known in the art. They can also be manufactured in plastic via an injection molding process, such as is as described for example in U.S. patent application Ser. No. 10/193,317, filed Jul. 12, 2002, which is hereby incorporated by reference.

The length and thickness of the microprotrusions are selected based on the particular substance being administered and the thickness of the stratum corneum in the location where the device is to be applied. Preferably, the microprotrusions penetrate the stratum corneum substantially without piercing or passing through the stratum corneum. The microprotrusions can have a length up to about 500 microns. Suitable microprotrusions have a length of about 50 to 500 microns. Preferably, the microprotrusions have a length of about 50 to about 300 microns, and more preferably in the range of about 150 to 250 microns, with 180 to 220 microns most preferred. The microprotrusions in the illustrated embodiment have a generally pyramidal shape and are perpendicular to the plane of the device. These shapes have particular advantages in insuring that abrasion occurs to the desired depth. In preferred embodiments, the microprotrusions are solid members. In alternative embodiments, the microprotrusions can be hollow.

Figure 3:
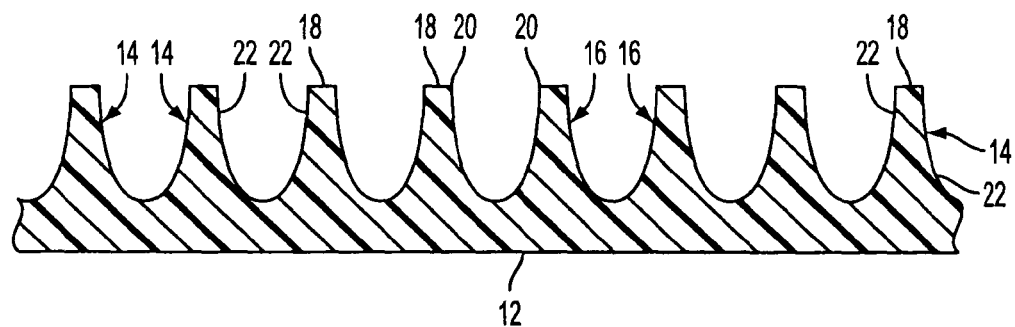
FIG. 3 is a cross sectional side view of an abrading surface.

As shown in the embodiment of FIGS. 3 and 5, the microprotrusions 14 are spaced apart uniformly in rows and columns to form an array for contacting the skin and penetrating the stratum corneum during abrasion. The spacing between the microprotrusions can be varied depending on the substance being administered either on the surface of the skin or within the tissue of the skin. Typically, the rows of microprotrusions are spaced to provide a density of about 2 to about 10 per millimeter (mm). Generally, the rows or columns are spaced apart a distance substantially equal to the spacing of the microprotrusions in the array to provide a microprotrusion density of about 4 to about 100 microprotrusions per $mm^2$. In another embodiment, the microprotrusions may be arranged in a circular pattern. In yet another embodiment, the microprotrusions may be arranged in a random pattern. When arranged in columns and rows, the distance between the centers of the microprotrusions is preferably at least twice the length of the microprotrusions. In one preferred embodiment, the distance between the centers of the microprotrusions is twice the length of the microprotrusions ±10 microns. Wider spacing is also included, up to 3, 4, 5 and greater multiples of the length of the microprotrusions. In addition, as noted above, the configuration of the microprotrusions can be such, that the height to the microprotrusions can be greater than the depth into the skin those protrusions will penetrate.

While FIG. 4 shows a partial microprotrusion array of abrading surface 5, it is envisioned that an abrading surface can be composed of a plurality of microprotrusion arrays. For example, four rectangular or square microprotrusion arrays can be used to make one abrading surface. In one embodiment, the microprotrusion array may be constructed of several smaller microprotrusion arrays so that the scraping edges 20 and 22 of each smaller microprotrusion array face a different direction in the larger, composite microprotrusion array. The asymmetrically opposed scraping edges (or scraping edges at differing angles) could maximize the abrasion by always presenting a scraping edge during the rotation of the abrading surface. A larger, composite microprotrusion array with this feature may be achieved by making a frustoconical microprotrusion array where the scraping edges are formed along the crystalline axis with the same orientation and then cutting the resultant frustoconical microprotrusion array in a number of smaller arrays and turning the smaller arrays so that the scraping edges have a different orientation than the adjacent smaller array. In order to provide an abrading surface that matches the skin contour, each array of the abrading surface may have varying microprotrusion heights to give a flexible platform effect while the abrading surface is rotated.

The abrading surface 5 can be rectangular, circular, or any other shape. Depending upon the drug or vaccine to be delivered and the amount of abrasion desired, the array of microprotrusions 14 on the abrading surface 5 may have varying designs that may be beneficial for rotary delivery devices. The tips of the microprotrusions may be in the same plane or their heights may vary due to the amount of abrasion desired. Each microprotrusion has at least one scraping edge and is of a length to penetrate the stratum corneum without piercing the stratum corneum, and depending on the desired amount of abrasion, the scraping edges of an array or portion of an array may point in the same or different directions.

The flat upper surface, or mesas of the frustoconical or frustopyramidal microprotrusions is generally 10 to 100, preferably 30–70, and most preferably 35–50 microns in width.

Figure 1:
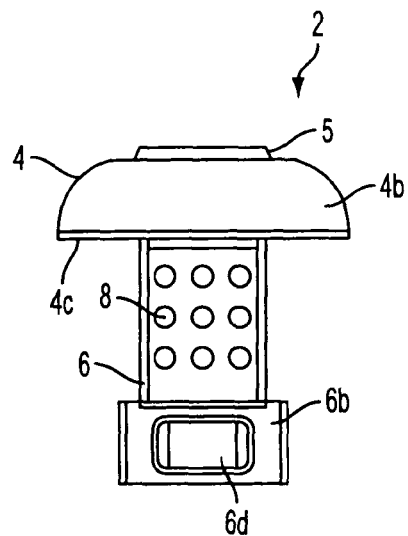
FIG. 1 is a side view of a microabrader that can be applied manually.

Manual microabrader device 2 of FIG. 1 is applied to a subject by grasping handle 6 and moving microabrader device 2 across a subject's skin 28 with enough pressure to enable abrading surface 5 to penetrate the outer protective skin or stratum corneum of the subject. The pressure applied to the base causes surface 5 and base 4 to be pressed into the subject's skin. Accordingly, it is preferred that the height of the sloping mushroom-like crown 4b be sufficient to prevent an applied substance from flowing over and onto underside 4c of base 4 when microabrader device 2 is being used.

A handle 6 is attached to arcuate base 4. Handle 6 may be glued (e.g., with epoxy) to the underside 4c of base 4, may be a snap or friction fit, or be integrally molded. Underside 4c of base 4 may be flush with mushroom-like crown 4b or extend beyond the mushroom-like crown, or may be integrally formed as an extension of base 4. The lower end 6b of handle 6 is wider than the shaft of handle 6. Lower end 6b includes an impression 6d that serves as a thumb rest for a person administering the substance to firmly grasp microabrader device 2. In addition, protrusions 8 are formed on the outside of handle 6 to assist a user in firmly gripping handle 6 when using the device 2 against a patient's epidermis.

The handle 6, as well as the base 4, of the microabrader device 2 is preferably molded out of plastic or the like material. The microabrader device 2 is preferably inexpensively manufactured so that the entire microabrader device and abrading surface can be disposed after its use on one patient.

One method of forming an abrading surface with microprotrusions is by etching a rectangular piece of silicon. The etching procedure provides a master abrading surface with a surface contour. As described below, the master abrading surface can become a mold for an abrading surface with an array of microprotrusions. The surface contour of the master is coated with a layer of material, the layer preferably having a thickness of at least about 0.01–0.2 inches and preferably 0.07 inches or greater. The master is removed from the layer of material to form a negative image of the master in the layer of material. The negative image may then be used in a molding process to form a positive image having features that are substantially the same as the features of the master.

The master is sacrificed when it is removed from the layer of material. For example, the master may be removed by etching. In another embodiment, the master is coated with a release layer, before being coated with the layer of material. The release layer facilitates removal of the master from the negative image, preserving the master unharmed.

Another method of forming an abrading surface with a plurality of microprotrusions involves using a master abrading surface having a surface contour defining a plurality of features. The surface contour of the master is coated with at least one layer of material to form a shell. The master is removed from the shell to form a negative image of the surface contour in the shell. The negative image in the shell is substantially filled with material, for example, polycarbonates (LEXAN® polycarbonate), acrylics (ACRYLITE® acrylic), COCs (Topas® Cyclic-Olefin Copolymers), polystyrenes, or other suitable structural plastic, to form a device having features substantially the same as the master. Of course, other types of materials may be used to fill the shell. The negative image may be filled using injection molding, compression molding, embossing or any other compatible technique.

In a further embodiment, the shell defines recesses having a depth of about 5 microns to about 250 microns. The recesses may be arranged in an array of uniformly spaced or non-uniformly spaced rows and columns or other patterns, including random patterns, to provide a density of about 4 to about 100 of the recess per $mm^2$. The shell is a negative or reverse image for molding the features of the master, where the master can have recesses or peaks on its surface contour ranging from about 0.5 micron to several hundred microns in length.

As described above, a method for delivering a substance into the skin of a patient can include the steps of coating a patient's outer skin layer with a medicament or other substance and rotating microabrader device 2 against the patient's skin to provide abrasions leaving furrows sufficient to permit entry of the substance into the patient's epidermis. Alternatively, the medicament or other substance may be applied to abrading surface 5 of microabrader device 2. The rotation is achieved mechanically or electronically with a device (FIGS. 7–15) that rotates the microabrader surface as described below. The rotation may be performed in either the clockwise and counter-clockwise direction, or both directions.

Figure 6:
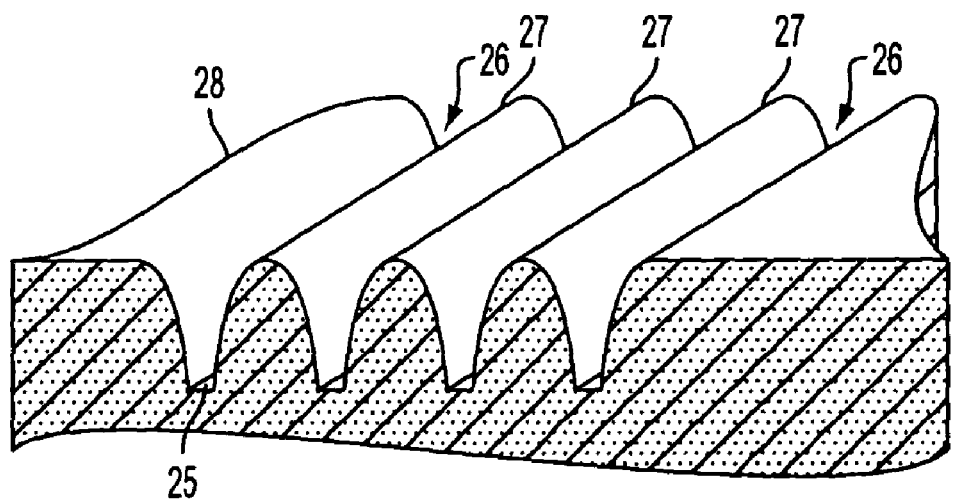
FIG. 6 is a perspective view in partial cross section of abraded furrows of skin.

In preferred embodiments of the microprotrusions, top surfaces or edges 20 (FIGS. 2 3, 4 and 5) of microprotrusions 14 abrade the outer protective skin layer by penetrating the stratum corneum forming grooves 26 (FIG. 6) thereby permitting medicament or other substances to enter the patient. In addition to edges 20, edges 22 of microprotrusions 14 also form scraping edges to aid in forming the grooves 26 or furrows in skin 28. As shown in FIG. 6, depending on the number of microprotrusions 14 and their arrangement on abrading surface 5, scraping edges 20 and 22 form open valleys 25 and scarified side walls 27 in the grooves 26. After the initial abrasion of the outer protective skin layer in a first circular direction, the trailing and leading edges of microabrader device 2 may also rub the surface of the abraded area working the medicament or substance into the abraded skin area thereby improving its interaction with the underlying epidermis.

Figure 7:
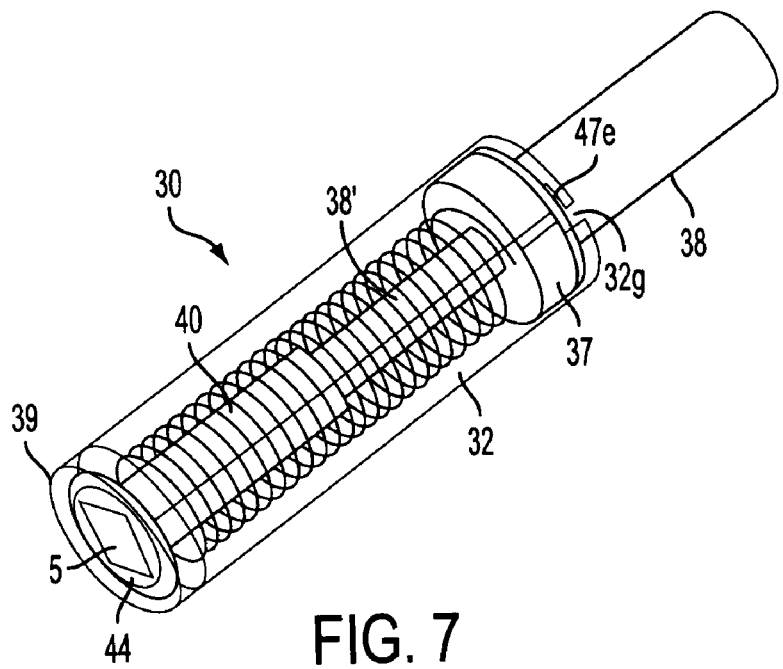
FIG. 7 illustrates a rotary delivery device containing abrading surfaces.
Figure 8:
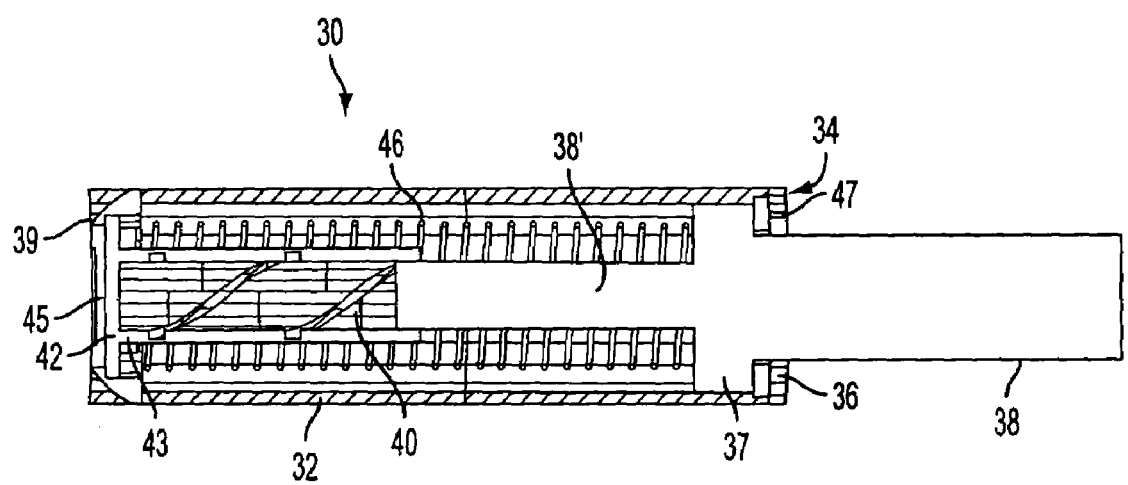
FIG. 8 illustrates a cross-sectional view of the rotary device of FIG. 7.

Looking at FIGS. 7 and 8, a rotary delivery device 30 is shown according to one embodiment of the invention. FIG. 7 is a perspective view of a device depicted with a see-through housing so that the mechanical components can be viewed, while FIG. 8 is a sectional view of rotary device 30. Rotary delivery device 30 includes a housing 32, which is cylindrical in this preferred embodiment. The housing need not be circular, as rectangular, square, oval or other shapes may be used. Housing 32 has a longitudinal axis, is generally hollow and is preferably of a shape about which a user's fingers can grasp for added control. The top 34 of housing 32 has an opening 36 through which an interlock mechanism, such as button 38 that is integrally attached to a longitudinally movable rod 38' moves upon activation. In a preferred embodiment, the top of button 38 extends through opening 36 while a base 37 of button 38 adjacent rod 38' is located inside housing 32. Base 37 has a larger width/diameter than the top of the base. The width/diameter of the base is approximately equal to the interior of housing 32. The thickness of base 37, as well as its width, is designed to provide a strong, stable support for the activation means or push button 38. Rod 38' preferably is integrally attached to the base 37 of button 38 inside of housing 32.

The other end 39 of rotary delivery device 30 is designed to be placed against a subject's skin and to remain stationary while button 38 is activated. Thus, end 39 of housing 32 serves to tension the skin of a subject prior to abrasion by an abrading surface 5. That is, the perpendicular force applied to the rotary delivery device provides a tight skin area to aid the abrading surface in scraping the skin area.

Located concentrically inside housing 32 and preferably recessed from end 39 of rotary delivery device is a hollow sleeve 40. Hollow sleeve 40 is freely rotatable within housing 32 and is formed with groove-like threads. The end of longitudinally movable rod 38' opposite the end attached to button 38 is inserted into the top end of hollow sleeve 40. Projections (not shown) extending from the end of longitudinally movable rod 38' extend into groove-like threaded areas of hollow sleeve 40. The threads are designed to transfer the longitudinal movement of button 38 and rod 38' into a rotary movement. Alternatively, the opposite end of rod 38' could be provided with a recess and hollow sleeve 40 could have raised threads in order to translate the longitudinal motion of rod 38' into the desired rotary movement. As a result of this structure, when button 38 is activated, rod 38' collapses inside hollow sleeve 40 along the thread grooves thereby causing hollow sleeve 40 to spin approximately 360 degrees through the full stroke of button 38.

An end face 42 is integrally formed at the end of hollow sleeve 40 near end 39 of rotary delivery device 30. In an alternative embodiment, an end face may be attached via adhesive or the like to hollow sleeve 40. An abrading surface 5, such as previously described, is attached to a front end 44 of face 42 of hollow sleeve 40. Abrading surface 5 can be retracted inside housing 32 before button 38 is pressed or activated. The curved portion of the groove-like threads can be designed so that the abrading surface 5 rotates approximately 360 degrees against a subject's skin when button 38 is depressed. Depending upon the drug or vaccine to be delivered, less rotation or multiple rotations of abrading surface may be desired. Since housing 32 remains stationary while button 38 is activated, housing 32 keeps the skin in place as abrading surface 5 abrades the area of skin inside stationary housing 32. Consequently, consistent, reproducible results as to the amount of drug or vaccine absorbed by a patient should be achieved.

Figure 7E:
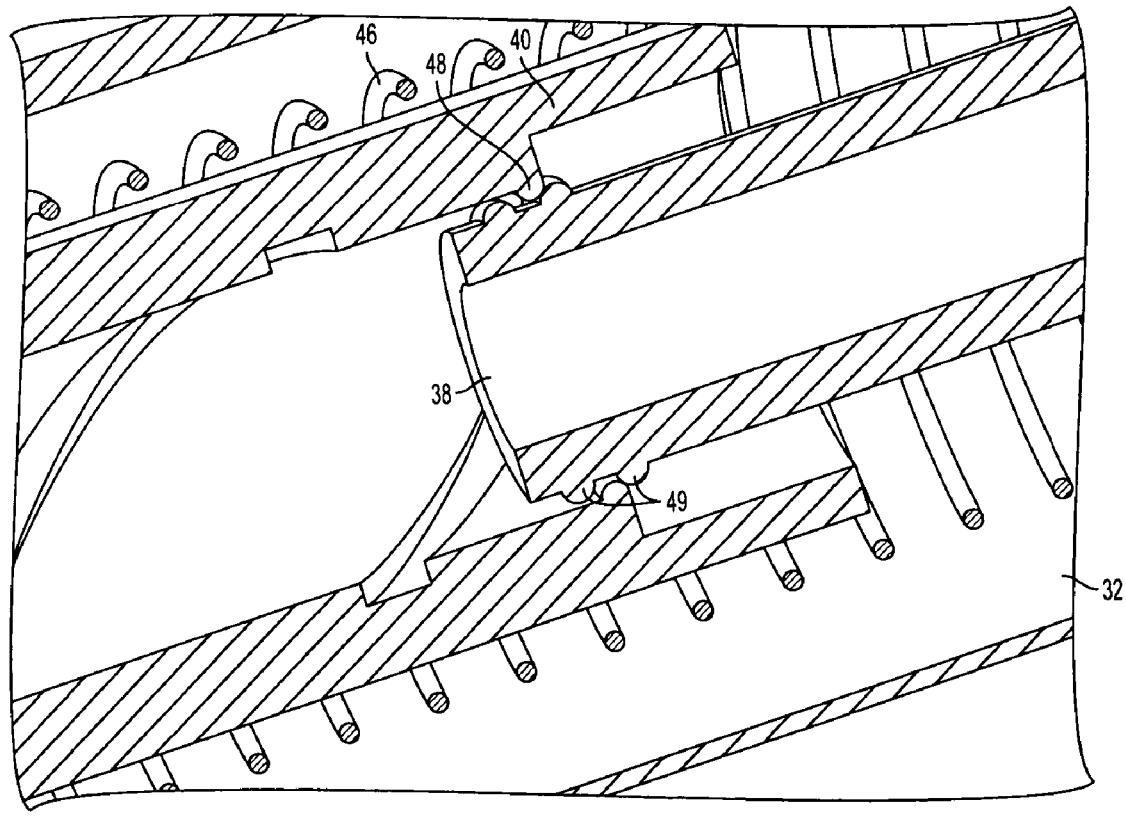
FIG. 7E is an exploded, cross-sectional view of a movable rod and hollow sleeve of a rotary device according to an embodiment of the invention

FIG. 7E illustrates one embodiment according to the invention in which the end of rod 38' and top of hollow sleeve 40 are designed to provide a safety retraction feature. The top of hollow sleeve 40 is provided with a projecting lip 48 and the end of rod 38' is provided with two projecting lips 49 that are spaced from one another. After the rotary delivery device has sufficiently abraded the desired area of skin, an operator pulls button 38 away from housing 32 causing one of the projecting lips 49 of rod 38' to move past projecting lip 48 of hollow sleeve 40 so that projecting lip 48 rests between the two spaced projecting lips 49 of rod 38'. In this manner, the hollow sleeve is pulled back within housing 32 and locked into this retracted safety position, as a large force would be necessary to move the hollow sleeve from the retracted safety position. This feature may also be used to push the device into the skin, as well as retract.

While the interlock mechanism illustrated is a button disposed perpendicularly to the abrading surface, other interlock mechanisms may be employed. For example, a lever disposed about the housing of the rotary device may be pushed approximately parallel to skin held in place by the stationary housing. The lateral pushing of the lever would deactivate a spring causing the abrading surface 5 held within the stationary housing to rotate. Similarly, a handle projecting from the side of the stationary housing may be a lever, button or rotary motion that deactivates the spring causing the abrading surface 5 to rotate.

Abrading surface 5 may be attached to front end 44 of hollow sleeve 40 via an intermediate ring 45, as shown in FIG. 8 or can be directly attached to front end 44 of hollow sleeve 40 via adhesive (FIG. 7). Depending upon the positioning of the threads in hollow sleeve 40, the abrading surface 5 may move slightly forward toward the front of housing 32. That is, the abrading surface 5 would be retracted inside the housing until button 38 is activated. Then, as rod 38' collapses inside hollow sleeve 40, hollow sleeve 40 and abrading surface 5 are pushed forward and rotated due to the threaded hollow sleeve. Thus, as the button 38 is pushed, the abrading surface 5 rotates against the subject's skin. The abrading surface 5 may be permanently attached to a disposable piece, or, the abrading surface may be disposed on a chip that can be snapped onto the ring 45 or another disposable piece. This will enable the chip to be replaced without having to reproduce the entire rotary delivery device. In another embodiment, the abrading surface 5 may also be made integral with end face 42 attached to hollow sleeve 40. In such an embodiment, the entire rotary delivery device would be disposable after abrading a single patient. The rotary delivery device 30 is envisioned for abrasion of more than one location on a single patient to deliver a vaccine or other substance and then can be disposed. It is also envisioned that the rotary device be modified to adapt to or otherwise mate with or accept a separate microabrader device instead of having the abrading surface 5 integral therewith.

A light spring 46, for example a 0.024" wire OD and 5 windings per inch, concentrically surrounds the rod 38' and hollow sleeve 40. As shown in FIG. 8, end face 42 of hollow sleeve 40 has a projecting rim 43 and light spring 46, in its extended state, extends from projecting rim 43 to base 37. The depression of button 38 compresses spring 46 so that device 30 will automatically reset when pressure is removed from button 38. That is, when button 38 is no longer depressed thereby releasing spring 46 from its compressed state, spring 46 applies an opposite load causing abrading surface 5 to rotate 360 degrees in the opposite direction. Button 38 can be pushed a number of times depending upon the amount of abrasion desired. This retracted abrading surface provides a safety disposal feature for the rotary delivery device.

For easy assembly of a rotary delivery device according to the invention, a retaining ring or washer 47 covers opening 36. In one embodiment, retaining ring 47 has two ears 47e on opposing sides of the ring, one of which is shown in FIG. 7. Ears 47e are received in grooves 32g at the top of housing 32 and are locked in place by turning the same. In another embodiment, the top of housing 32 would be provided with a cap with an opening that receives button 38. The cap would be screwed onto housing 32. Thus, one could easily assemble spring 46, hollow sleeve 40, rod 38' and button 38 inside housing 32 and then lock the assembly together. Retaining ring 47 or a screw cap would hold the above components inside housing 32, even when spring 46 was released. The housing 32, hollow sleeve 40, rod 38' and button 38 are made from a plastic material, which can be easily molded into the particular shapes.

Figure 9:
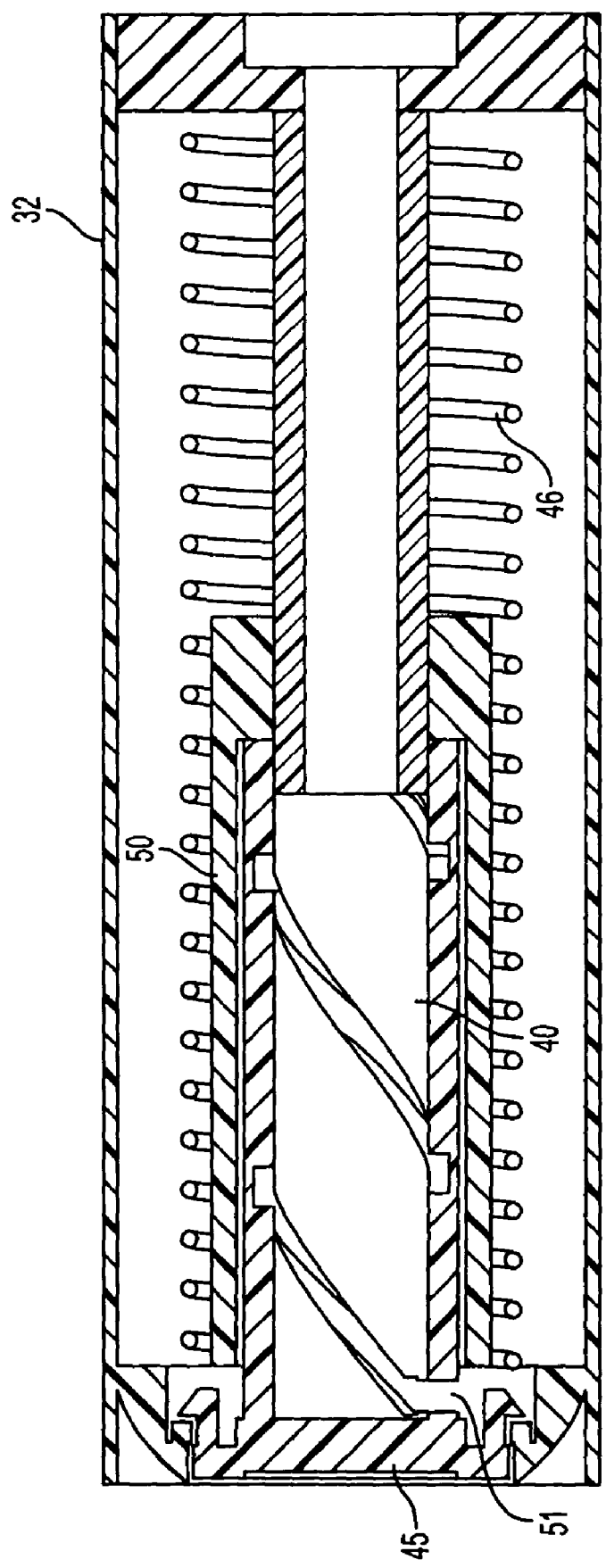
FIG. 9 is a schematic view of a portion of another embodiment of a rotary delivery device containing a safety retraction feature.
Figure 10:
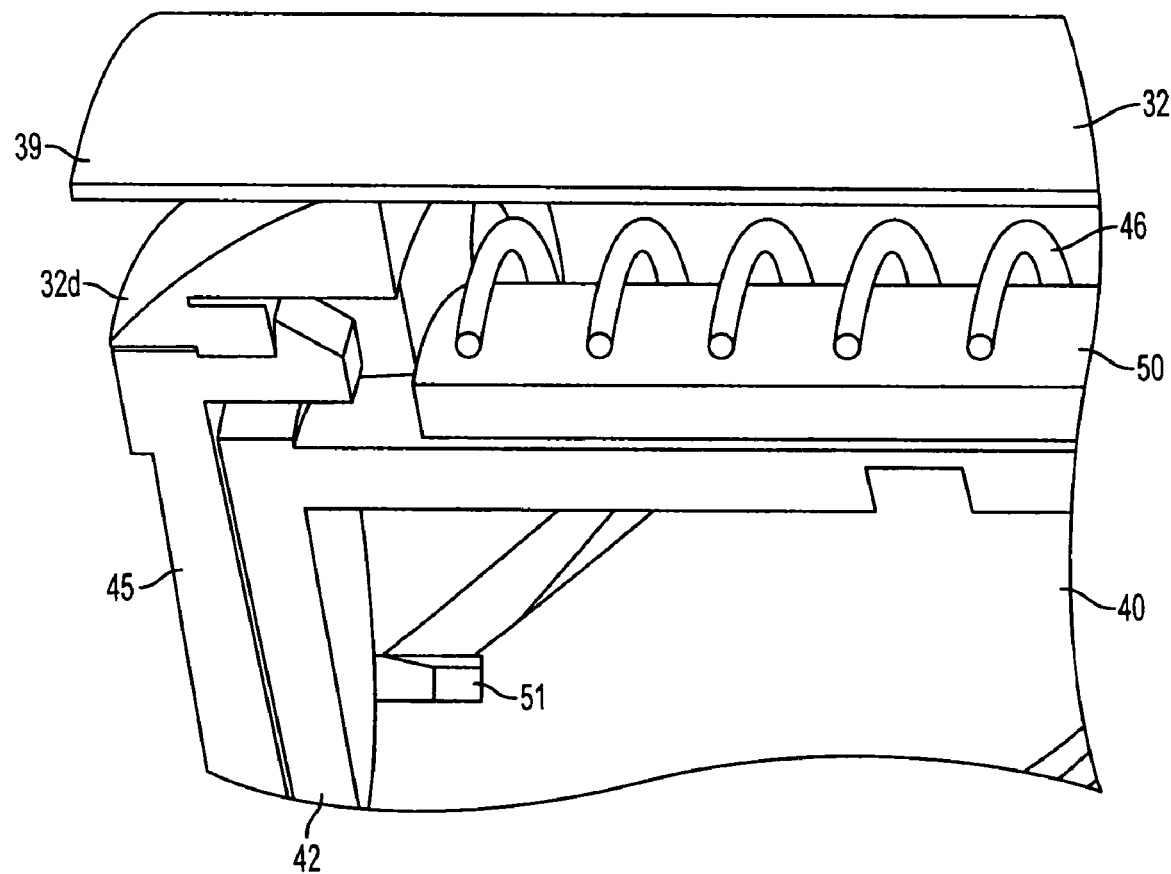
FIG. 10 is a close-up, schematic view showing a stop in the device of FIG. 9.

The retraction of the abrading surface 5 within housing 32 can be achieved via a layer of cushion 50 concentrically formed about the lower end of rod 38 and the upper end of hollow sleeve 40 as shown in FIGS. 9 and 10. Cushion 50 is of a height so that a full stroke of button 38 can be achieved before base 37 reaches the top of cushion 50. A technician using the rotary delivery device would feel the resistance of the cushion and this tactile sensation would indicate that the technician should release button 38 causing abrading surface 5 to rotate in the opposite direction. After the appropriate amount of revolutions resulting in the desired amount of abrasions, the technician would push button 38 past the initial resistance of cushion 50 so that the projections of rod 38' lock into recesses 51 in the groove-like threads of hollow sleeve 40. The cushion 50 then pulls the abrading surface 5 into the housing 32 as a safety feature.

As shown in the enlarged portion of the embodiment in FIG. 9, recess 51 may be located adjacent end face 42 at the end of a groove-like thread. Light spring 46 surrounds cushion 50, which is recessed in housing 32, and extends from a flange of ring 45 to base 37 of button 38. After the projections at the tip of rod 38' are locked into the recesses 51 of hollow sleeve 40, the technician could pull button 38 away from end 39 thereby retracting hollow sleeve 40, ring 45 and abrading surface 5 inside housing 32. Specifically, the flange of ring 45 would be pulled into cushion 50 deforming the cushion about the flange resulting in the cushion 50 holding ring 45 and abrading surface 5 within housing 32. The material of cushion 50 may be foam or the like to provide for engagement of the feature which keeps the abrading surface retracted after rotary delivery of a substance via abrasion on a patient.

Alternatively, it is envisioned that a second spring (not shown) with a greater compression strength than light spring 46 could be employed to enable button 38 and rod 38' locked in hollow sleeve 40 to be retracted inside housing 32. Such an embodiment would enable the rotary delivery device to provide multiple rotations of the abrading surface and retract inside housing 32.

In a preferred embodiment housing 32 would have a domed flange 32d, which may be integral with housing 32. This domed flange would provide stability to ring 45 so the same would not tilt or tip during the rotary motion. The second spring may be located outside light spring 46 with one end at the top of dome flange 32d and the other end of the second spring extending to base 37 in its relaxed state.

In another embodiment, light spring 46 may have a diameter such that one end of the spring reaches the top of dome flange 32d and the other end extends to base 37 in the relaxed state. This embodiment, when employed with the cushion retracting feature described above would result in a one rotation rotary delivery device with a retractable feature would be achieved. Specifically, a technician would push button 38 driving rod 38' along the groove-like threads of hollow sleeve 40 causing hollow sleeve 40 and the abrading surface 5 to rotate. The projections of rod 38' could be pushed into recesses 51 locking hollow sleeve 40 with rod 38'. When the technician stops applying pressure to button 38, spring 46 would expand into its relaxed state causing abrading surface 5 and hollow sleeve 40 to be retracted inside housing 32.

Figure 2:
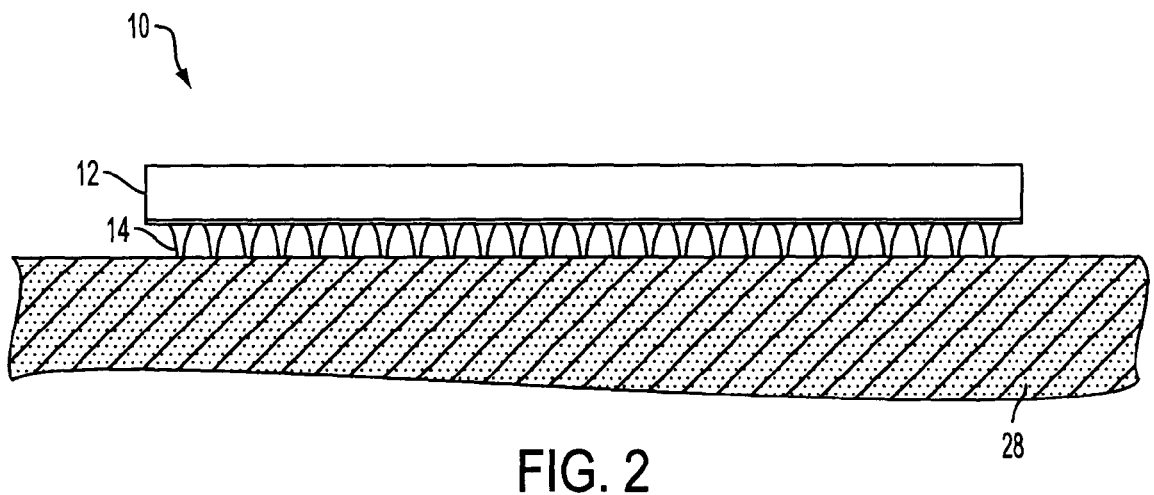
FIG. 2 is an exploded side view of an abrading surface for an abrader array according to one embodiment of the invention on the skin of a patient.

In another embodiment, a detent 51 formed at the bottom of button 38" may be used to secure the abrading surface within the housing after the desired amount of abrasion is achieved. This embodiment is schematically illustrated by FIGS. 9 and 10. A coupler is used to mate a microabrader device with a handle to button 38". Any type of coupler is envisioned that can join the handle of a microabrader device with a button that can be rotated within a housing. The coupler could mate a microabrader device, for example, as shown in FIGS. 1–2 with button 38". The size of the detent 51 compared to the opening 36' is designed to ensure that a technician or user applying the microabrader device applies sufficient force to button 38", while force detent 51 through opening 36'. That is, a predetermined amount of force would be necessary to force the button toward the subject's skin. In one embodiment, button 38" may be activated by this predetermined force and then is rotated mechanically (using a torsion spring, for example) causing abrading surface 5' of a microabrader device to spin while being applied against the subject. The force of the torsion spring causing rotation would result in the appropriate amount of abrasion to the subject's skin.

In another embodiment, after push button 38" is pushed through hole 36', manual rotation of button 38" could cause abrading surface 5' to rotate. A light spring 46' surrounding the rod attached to button 38' and disposed inside housing 32' would compress when button 38" is pushed so that upon release of button 38", the abrading surface would rotate in the opposite direction, as described above. However, detent 51 would stop at the top 34' and the technician or user would have to pull detent 51 through opening 36'. This is a safety feature according to the invention, as the abrading surface of the rotary delivery device would be retracted inside housing 32' and remains retracted for safe disposal.

Applicants have determined through experimentation that in order for the microabrader device to produce repeatable results and to deliver the appropriate dose of substance or medicament to the within the epidermal layer of a patient, sufficient control of the amount of pressure applied to the microabrader device is required. According to the invention, the microabrader array surface 5 should optimally only disrupt the stratum corneum. If too much pressure is applied, the microabrader device may remove too much of the epidermal layers. On the other hand, if not enough pressure is applied, the microabrader surface may not penetrate the stratum corneum. This under abrasion may result in not enough substance or medicament being delivered to the body. Control of the pressure being applied aids in determining the depth of penetration, as well as the amount of force to achieve the desired penetration and the desired abrasion. Methods and devices to control the abrasion process are fully described in applicant's co-pending U.S. application Ref# P-5370, previously incorporated by reference.

Figure 11:
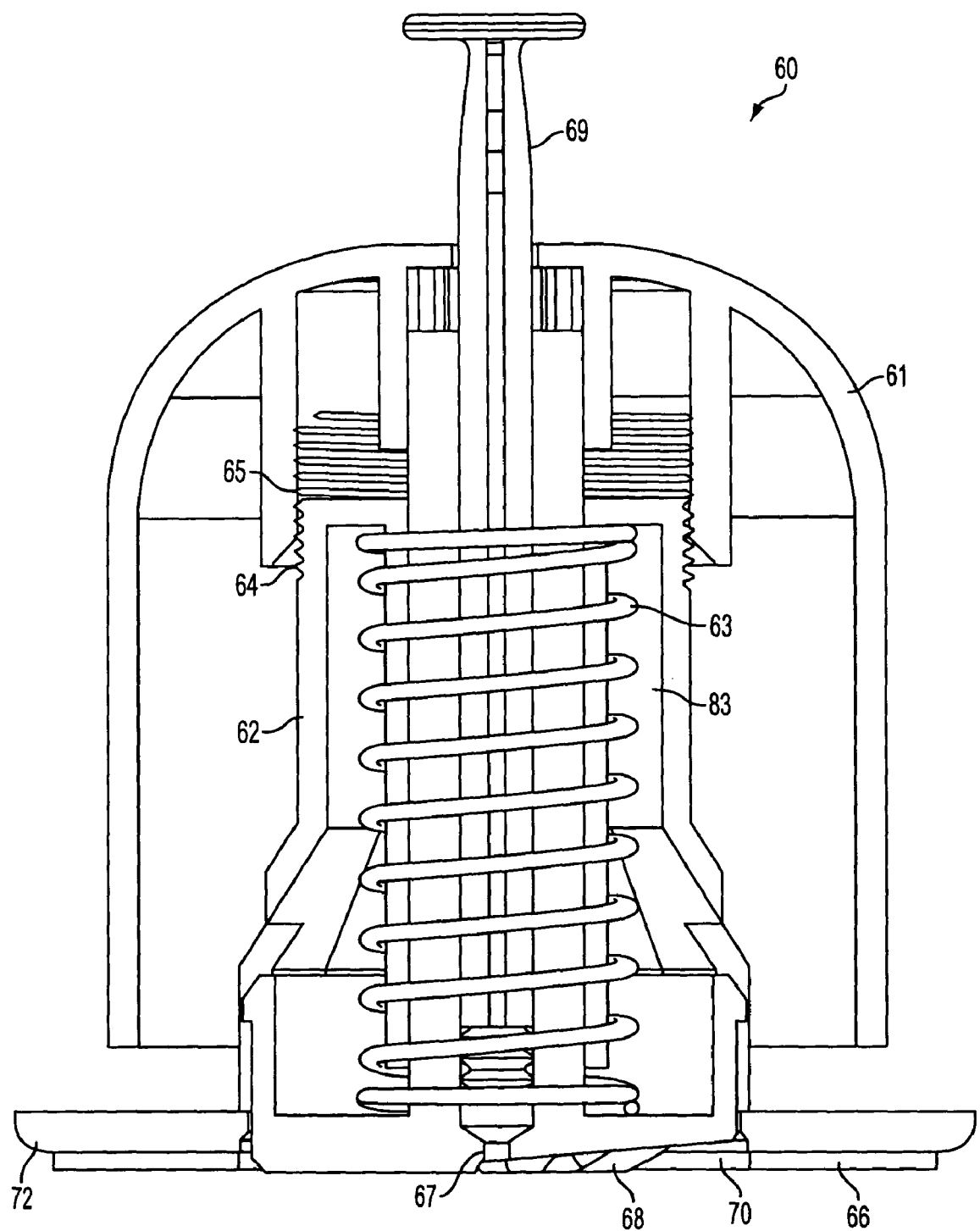
FIG. 11 is a cross-sectional, schematic view of another embodiment of a rotary microabrader.

In yet another embodiment of the present invention a rotating abrading device is shown in the cross-sectional outline view of FIG. 11. To operate the user removes a cap (not shown), which protects an adhesive surface 66 and plugs the fluid port 67 during storage. The device 60 is pressed against the skin, which compresses the spring 63 and applies a predetermined pressure to the abrader surface 68. The adhesive 66, preferably of medical grade, holds the device 60 against the skin with more force than the pressure exerted by the spring 63. The plunger 69 is then depressed, which injects a liquid substance, e.g., a vaccine, drug, diluent, etc., into the fluid reservoir 70 formed by the seal of the adhesive 66 around the abrader surface 68. The abrader surface 68 has fluid channels 71 between the microabrader surfaces 68, and is essentially immersed in the medicament bath during use. The user then rotates the drive cap 72 in a clockwise direction until it can't be rotated any further. The number of turns is pre-determined by the number of threads 65 and 64 between the drive cap 61 and the base 62, respectively. The device 60 is then peeled from the skin and discarded.

Figure 12:
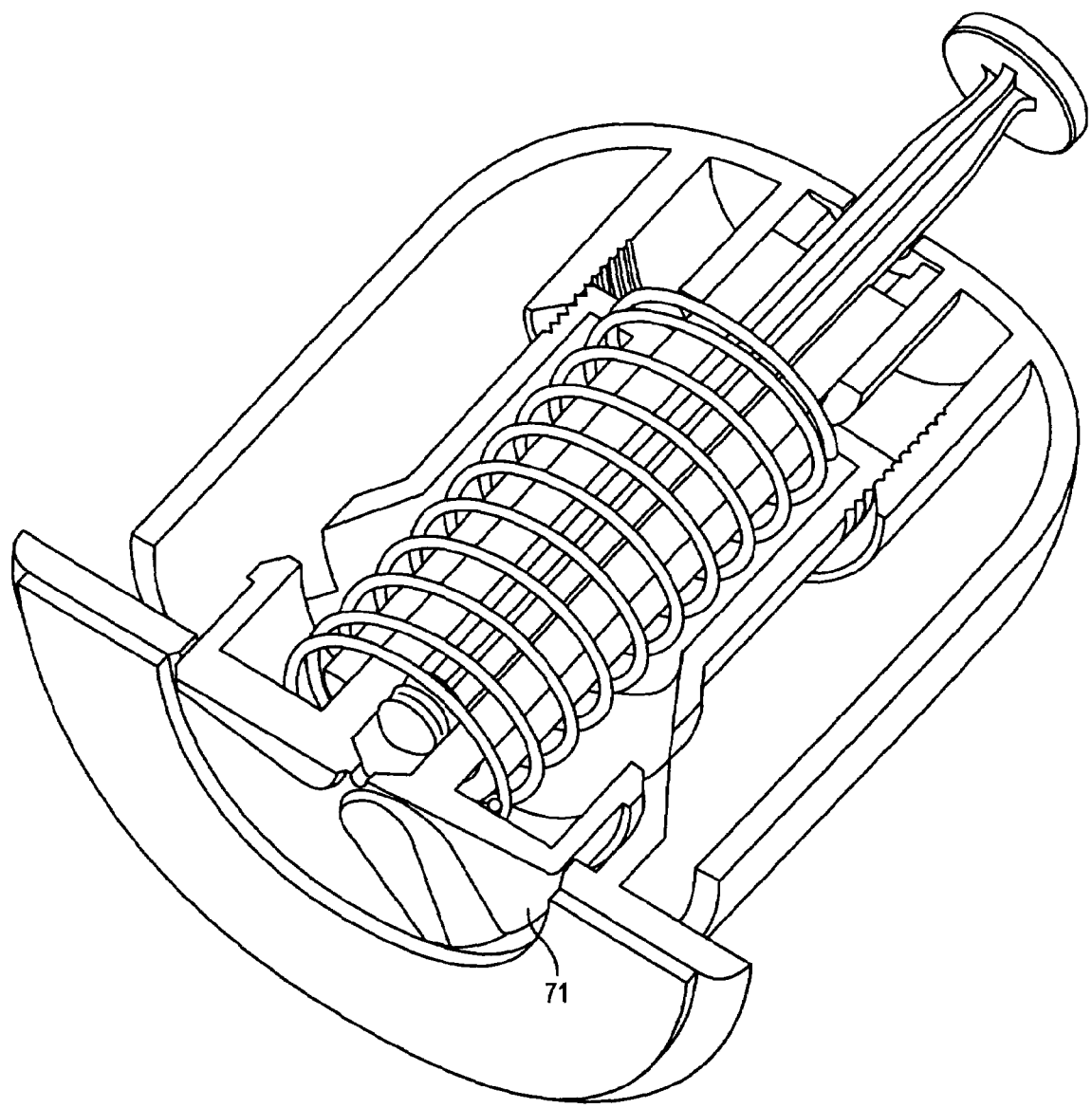
FIG. 12 is a cross-sectional, perspective view of the internal and abrading end of the device of FIG. 11.
Figure 13:
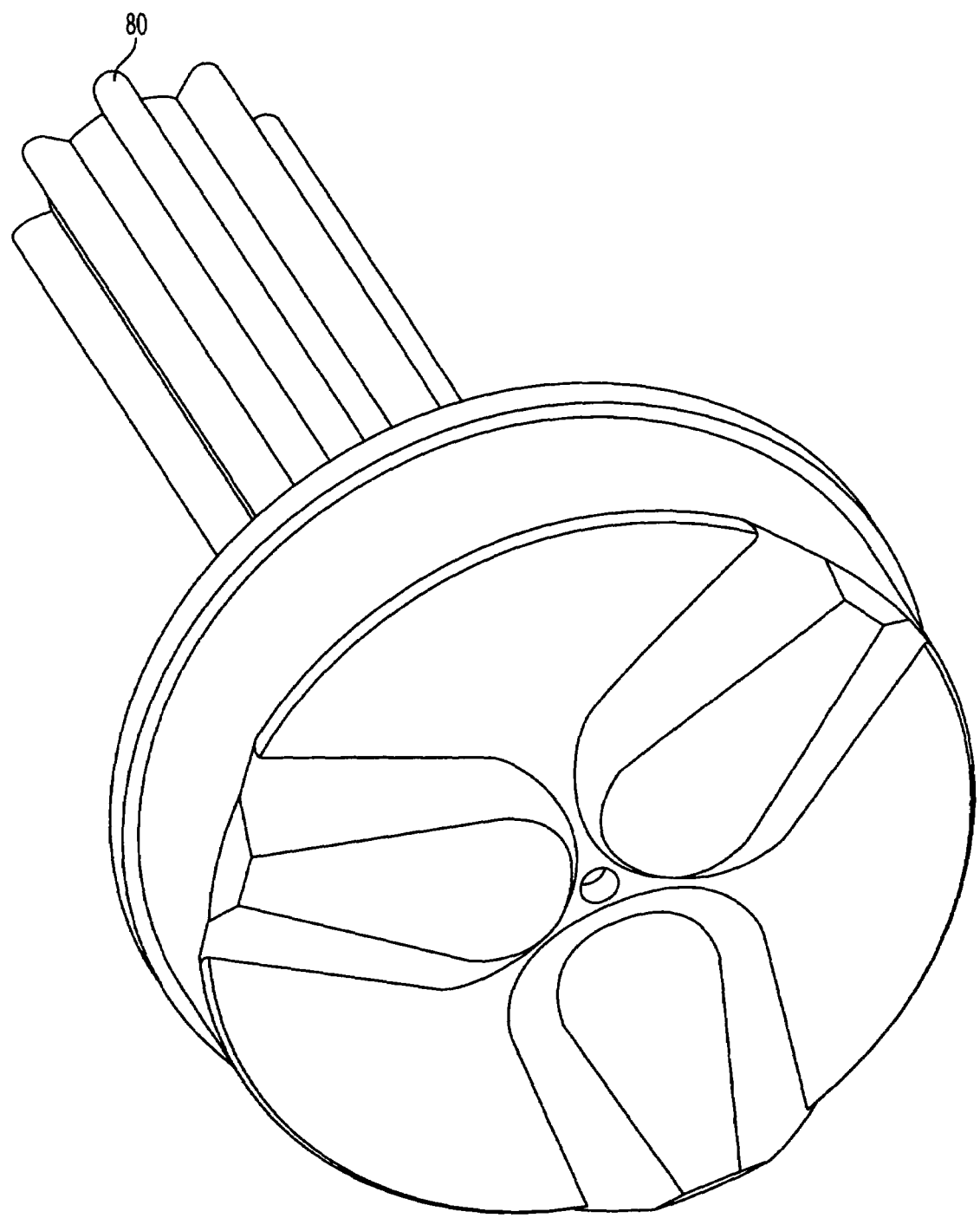
FIG. 13 illustrates the abrading surface assembly of device of FIGS. 11 and 12.

To ensure a more even abrasion of the stratum corneum the abrader surfaces 68 have a reverse taper, which provides for an equal swept area at every radius. FIGS. 12 and 13. Various designs and configurations of microprotrusions which are fully described in applicant's co-pending U.S. application P-5369B, previously incorporated by reference can be affixed or integrally formed on the abrader surface 58.

Figure 14:
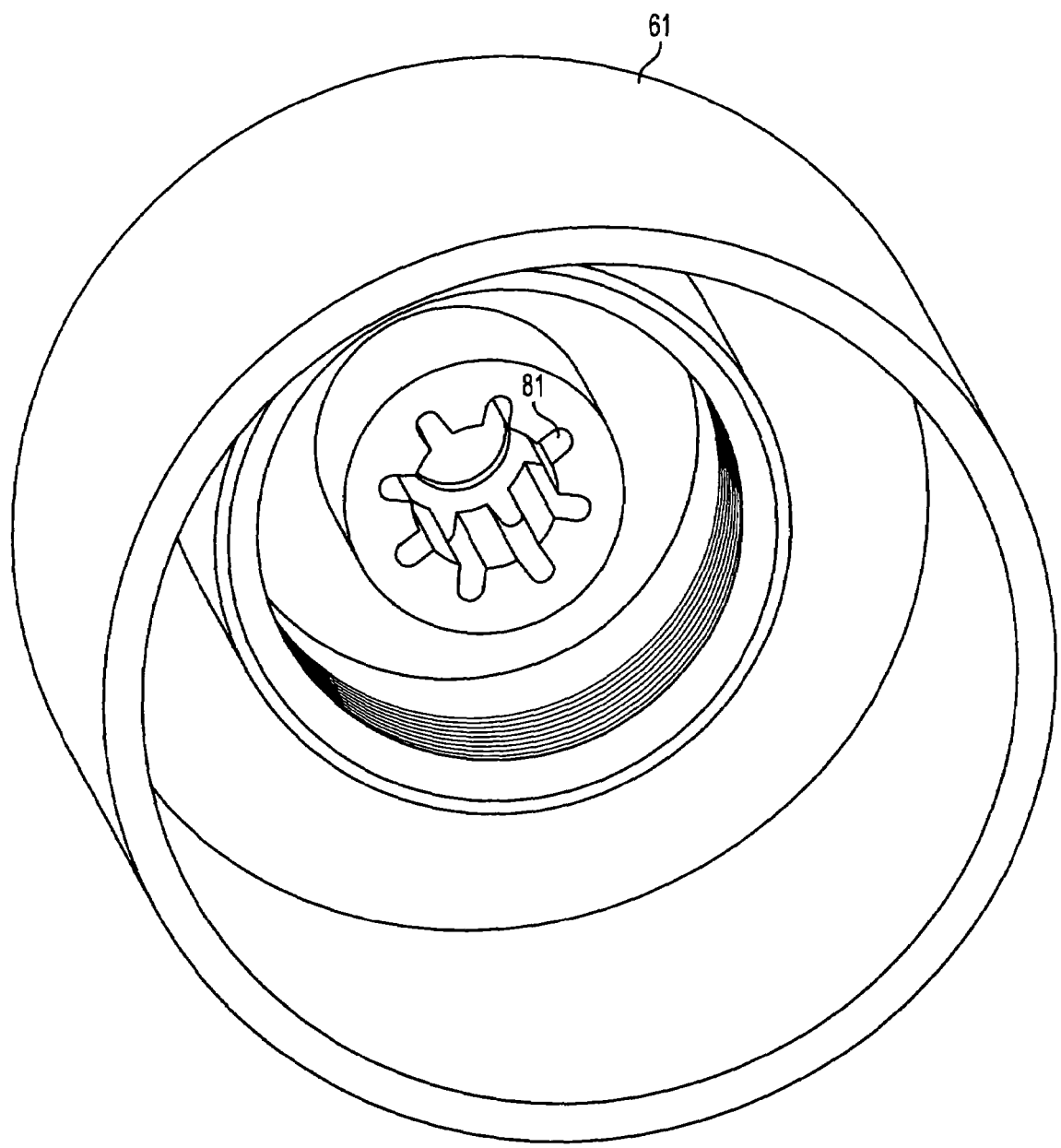
FIG. 14 illustrates the interior of the drive cap of the device of FIGS. 11 and 12.
Figure 15:
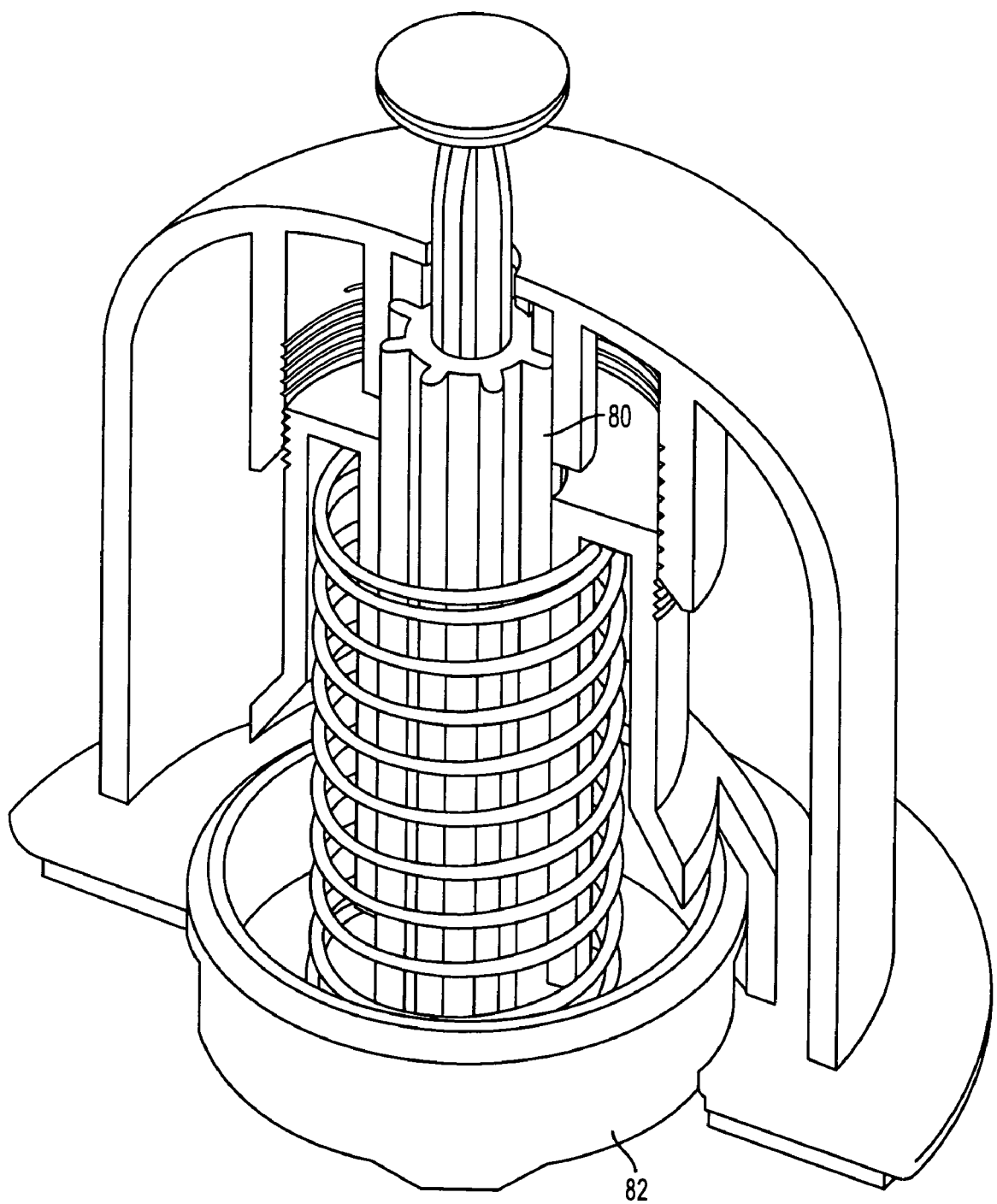
FIG. 15 illustrates a second perspective view of the abrading surface assembly of FIG. 13.

Preferably abrader assembly 72, FIG. 13, can be snap-fit into the base 62, FIGS. 12, 14 and 15, and will preferably extend from about to 0.1 mm about 4 mm beyond the adhesive surface 66 prior to use. Preferably it will turn freely inside the base 62 through opening 83 in base 62. Drive splines 80 on the abrader assembly 82 engage spline receiving elements 81 in the drive cap 61, which is used to rotate the abrader. The drive cap 61 will then move downward along the abrader splines 80 as it's turned onto the base threads 65. It is envisioned that a feature that would prevent the drive cap 61 from being inadvertently rotated counter clockwise off the base 62 could be integrated or added to the design of the microabrader 60.

It is also envisioned, and within the scope of the invention, that various other designs can be adapted to activate or enable the rotary action of the device. Some such examples, could be a through hole to allow the drive cap 61 to be rotated like a rotary telephone dial, a drive key, or a pair of "ears" or flanges could be provided to allow the drive cap to be rotated.

A plunger 69 or other fluid dispensing components can be provided with the assembled microabrader 60. Several fluid containing elements are envisioned to retain, store and preserve the substance to be administered or a diluent, if the abrader surfaces 68 are coated with a dried substance. For example, a glass or polymeric vial could be utilized, or a standard insulin cartridge, or a Blister-type reservoir, or a flexible reservoir. Any fluid-containing reservoir known in the art could be employed.

Applicants additionally envision an electronic rotary delivery device. In such a device, a piezoelectric chip is employed to rotate the microabrader array surface. Such a device would preferably have a spring to determine the amount of downward force applied against a subject's skin in addition to the electronics necessary to rotate the microabrader array surface. In addition, the spring may control the speed of the rotation of the abrading surface and the spring value would be set to optimally effect abrading of the skin.

The preferred method and rotary device would be placed against a subject's skin and then a button would be pressed to force the microabrader array device against the skin in a circular fashion, while a housing of the device remains stationary on the subject's skin. As described above, the rotation may be achieved manually, mechanically or electronically and the downward force applied may be controlled by pre-tensioned spring, the technician or electronically via a pressure transducer.

In one preferred method of abrading skin using circular motion, the microabrader device 2 can be rotated across a patient's skin at least two approximate full rotations. That is, the first approximate full rotation could be clockwise, while the second approximate full rotation is counter-clockwise or vice versa. The patient's skin may be abraded in opposite rotational directions. In other embodiments, the microabrader device may be rotated approximately 180° against the skin in either direction. The structural design of the microarray of the microabrader device according to the invention enables the medicament or substance to be absorbed more effectively thereby allowing less of the medicament or substance to be applied to a patient's skin or coating abrading surface 5.

Depending upon the substance or medicament being applied using the microabrader device, differing microprotrusion arrays forming the abrading surface may perform better. It will be understood that the above description of the present invention is susceptible to various modifications, changes and adaptations, and the same are intended to be comprehended within the meaning and range of equivalents of the appended claims.

We claim:

1. A method for delivering substance into skin via an abrasion device comprising the steps of:
    providing an abrader having a plurality of microprotrusion arrays, each array having a plurality of frustoconical protrusions, each protrusion having at least one scraping edge, wherein the frustroconical protrusions within each individual array have aligned scraping edges and each array is positioned within the abrader such that the scraping edges of each array are not aligned with the scraping edges of another array;
    positioning the abrader device at a delivery site on the skin of a patient;
    applying a substance to the skin of a patient at the delivery site; and,
    mechanically rotating the protrusions of the abrader device against the skin with sufficient force to disrupt and substantially penetrate the stratum corneum of the skin, thereby creating intersecting furrows in the skin by the rotation of scraping edges of the abrader.

2. The method according to claim 1, wherein the mechanical rotation of the protrusions forms an abraded area that increases the permeability of the skin to the substance and permits transfer of the substance through the abraded area into the skin.

3. The method according to claim 1, further comprising the step of providing a housing that surrounds the mechanically rotating protrusions, where the housing, which remains stationary during the rotation of the protrusions, keeps the skin of a patient, at the delivery site, taunt.

4. The method according to claim 3, wherein the housing holds the patient's skin at the delivery site in place as the protrusions of the abrader device are rotated against the skin to be treated.

5. The method according to claim 1, further comprising the step of monitoring the force with which the protrusions on the abrader device is applied against the skin.

6. The method according to claim 1, wherein the substance is applied on the skin of the patient at the delivery site before the abrader device is positioned at the delivery site.

7. The method according to claim 1, wherein the substance is applied on the skin of the patient at the delivery site simultaneously as the abrader device is positioned at the delivery site.

8. The method according to claim 1, wherein the substance is pre-applied or coated on the protrusions before the abrader device is mechanically rotated.

9. The method according to claim 1, wherein the rotation of the array of microprotrusions forms circular furrows, and some of the furrows intersect other furrows thereby increasing the amount of surface area through which the substance can be absorbed.

10. The method according to claim 1, wherein the mechanical rotation of the protrusions is about an axis substantially perpendicular to the skin.

11. The method according to claim 10, further comprising the step of translating said protrusions along said axis while rotating said protrusions about said axis, thereby disrupting the skin with both a rotating and translating motion.

12. A method for delivering substance into skin via a microabrader device comprising the steps of:
    positioning the microabrader device at a delivery site on the skin of a patient, said microabrader device having a support and a plurality of microprotrusion arrays, each array having a plurality of frustoconical microprotrusions coupled to the support where each of said microprotrusions having at least one scraping edge and a length to abrade the stratum corneum wherein the frustroconical protrusions within each individual array have aligned scraping edges and each array is positioned within the abrader such that the scraping edges of each array are not aligned with the scraping edges of another array; and rotating the microabrader device against the skin at the delivery site with sufficient force so that the plurality of microprotrusions disrupt and penetrate the stratum corneum substantially without piercing the stratum corneum thereby creating intersecting furrows in the skin by the rotation of scraping edges of the abrader and allowing a substance to be delivered into the skin of a patient at the delivery site.

13. The method according to claim 12, wherein the rotating step is accomplished by mechanically rotating the microabrader device.

14. The method according to claim 13, wherein the rotating step abrades a localized area of skin thereby increasing the resultant efficiency of drug or vaccine delivery.

15. The method according to claim 12, wherein the rotation of the protrusions is about an axis substantially perpendicular to the skin.

16. A method for delivering substance into skin via an abrasion device comprising the steps of:

providing an abrader having a plurality of microprotrusion arrays, each array having a plurality of frustroconical protrusions with at least one scraing edge wherein the frustroconical protrusions within each individual array have aligned scraping edges and each array is positioned within the abrader such that the scraping edges of each array are not aligned with the scraping edges of another array;

positioning the abrader device at a delivery site on the skin of a patient;

applying a substance to the skin of a patient at the delivery site; and, mechanically rotating the protrusions of the abrader device against the skin with sufficient force to disrupt and substantially penetrate the stratum corneum of the skin, wherein the rotation is about an axis substantially perpendicular to the skin, thereby creating intersecting furrows in the skin by the rotation of scraping edges of the abrader.

17. The method according to claim 16, wherein the mechanical rotation of the protrusions forms an abraded area that increases the permeability of the skin to the substance and permits transfer of the substance through the abraded area into the skin.

18. The method according to claim 16, further comprising the step of providing a housing that surrounds the mechanically rotating protrusions, where the housing, which remains stationary during the rotation of the protrusions, keeps the skin of a patient, at the delivery site, taunt.

19. The method according to claim 18, wherein the housing holds the patient's skin at the delivery site in place as the protrusions of the abrader device are rotated against the skin to be treated.

20. The method according to claim 16, further comprising the step of monitoring the force with which the protrusions on the abrader device is applied against the skin.

21. The method according to claim 16, further comprising the step of translating said protrusions along said axis while rotating said protrusions about said axis, thereby disrupting the skin with both a rotating and translating motion.

22. The method according to claim 21, further comprising the step of providing a housing that surrounds the mechanically rotating and translating protrusions, wherein the housing, which remains stationary during the rotation and translation of the protrusions, keeps the skin of a patient, at the delivery site, taunt.

23. The method according to claim 21, further comprising the step of monitoring the force with which the protrusions on the abrader device is applied against the skin.

24. The method according to claim 21, wherein the housing holds the patient's skin at the delivery site in place as the protrusions of the abrader device are rotated against the skin to be treated.

* * * * *